United States Patent [19]

Fischer

[11] Patent Number: Plant 6,645

[45] Date of Patent: Mar. 7, 1989

[54] AFRICAN VIOLET PLANT NAMED SWEETHEART

[76] Inventor: Arnold Fischer, Kahlendamm 22, 3000 Hannover 51, Fed. Rep. of Germany

[21] Appl. No.: 85,122

[22] Filed: Aug. 13, 1987

[51] Int. Cl.[4] ..... A01H 5/00

[52] U.S. Cl. ..... Plt./69

[58] Field of Search ..... Plt. 69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A cultivar of African violet named Sweetheart, characterized by its large single bicolor flowers which are mainly pale pink-lavender with a darker lavender-pink on the edges, medium green leaves, compact habit, and by its floriferousness.

1 Drawing Sheet

The present invention comprises a new and distinct cultivar of African violet plant, botanically known as *Saintpaulia ionantha,* named Sweetheart.

The new cultivar is a product of a planned breeding program carried out by applicant in Hannover, Federal Republic of Germany. The basic objective of the breeding program was to create a new African violet cultivar having single, pink and white bicolored flowers, medium green foliage, compact growth habit, and a highly floriferous habit.

The new cultivar was originated from a cross made by applicant in the controlled breeding program in Hannover, Federal Republic of Germany. Both the female (or seed) and the male (or pollen) parents were unnamed seedlings not specifically identifiable.

Sweetheart was discovered and selected by applicant as a flowering plant within the progeny of the stated cross in a controlled environment in Hannover, Federal Republic of Germany. Asexual reproduction of the new cultivar by leaf cuttings, as performed by applicant at Hannover, Federal Republic of Germany, has demonstrated that the combination of characteristics as herein disclosed for the new cultivar are firmly fixed and retained through successive generations of asexual reproduction.

Sweetheart has not been observed under all possible environmental conditions. The phenotype may vary significantly with variations in environment such as temperature, light intensity and day length. The following observations, measurements and values describe the new cultivar as grown in Parrish, Fla. under greenhouse conditions which closely approximate those generally used in commercial practice.

The following traits have been repeatedly observed and are determined to be basic characteristics of Sweetheart, which in combination distinguish this African violet as a new and distinct cultivar:

(1) Large purple single zygomorphic rotate flowers with a slightly ruffled margin, 33–37 mm in diameter.

(2) Primarily flowers have a pale pink-lavender background with a darker lavender-pink edge or picotee. Occasionally flowers display a solid darker lavender-pink color or display a light pink background with the darker color at the center of the flower.

(3) Medium green pubescent foliage, oval shaped with a cordate base, repand margin and broadly acute apex.

(4) Compact rosette habit with flowers held erect on strong upright peduncles.

(5) Very floriferous, with flowers continuing to open for many weeks after the onset of flowering.

(6) Suitable for production in 10 cm pots, finishing in 9–13 weeks when started from a 2¼" plantlet.

The new cultivar is similar in certain characteristics to Fairy Queen, disclosed in U.S. Plant Pat. No. 4,935. Sweetheart is principally distinguished from Fairy Queen by its wider picotee of varying color and less ruffled petal margin and leaves.

The accompanying photographic drawing shows a typical specimen plant of the new cultivar. The photograph is in black and white, with certain flowers being colored to accurately depict the color values noted below.

In the following description, color references are made to the Royal Horticultural Society Colour Chart (RHS), except where general colors of ordinary significance are referred to. Color values were taken under fluorescent light conditions at approximately 4:00 p.m. in Parrish, Fla.

Botanical classification: *Saintpaulia ionantha,* Ramat., cv. Sweetheart.

Parentage: Unknown.

Propagation: The new cultivar holds its distinguishing characteristics through successive propagations by leaf cuttings.

Plant: From 7 cm to 12 cm tall when grown in pots, and approximately 21 cm in diameter when fully grown. The growth rate is vigorous, and the general shape of the fully grown plant is round.

*Leaves.*—Quantity: Abundant. Shape: Oval with repand margin, cordate base and broadly acute apex. Diameter: up to 7.5 cm on a mature leaf. Texture: Pubescent, glossy. Ribs and Veins: Pinnate. Color (upper side): 137 A. Color (under side): 138 D. Petioles: Light green.

*Flowers.*—Buds: Size: About 1 cm×1 cm. Shape: Round. Rate of opening: Normal. Sepals: Shape: Lanceolate. Color: 141 D. Phyllaries: 2, lanceolate. Color: 137 A. Calyx: Shape: Funnel. Size: About 12 mm in diameter. Aspect: Pubescent. Peduncle: Length: up to 9 cm. Character: Erect, rigid. Color: Light green. Individual flowers: Number of petals: 5. Size: Approximately 35 mm in diameter and 8 mm deep. Shape: Cup shaped when bloom first opens, becoming flat as bloom matures. Color (upper side): Background color mainly 69C, with edge or picotee and center 82 B-C. Color (under side): Main color 69 C-D, edge and center 82 B-D. Flowers fade slightly as they age. The flower color may vary somewhat depending upon the amount of light, fertilizer, temperature and other growing conditions. Borne: Cymose clusters on upright peduncles, up to 9 cm long. Flowering Habit: Flowers profusely and intermittently year round, with blooms lasting 2–3 weeks after which petals dry up but do not drop. Finishes in 9–12 weeks when a 2¼" plantlet is placed in a 10 cm pot.

*Reproductive organs.*—Stamens: Stamens borne singly on one side of ovary. 2 anthers basifixed.

Anthers: 2 mm × 2 mm, yellow. Filaments: 3 mm, yellow with purple streaks. Pollen Color: Yellow. Pistels: Number: 1. Styles: 1, 6–7 mm long. Stigma: Sticky, white. Ovaries: Superior. Roots: Fibrous and fine.

Disease resistance: No African violet diseases observed to date.

I claim:

1. A new and distinct cultivar of African violet named Sweetheart, as illustrated and described, and particularly characterized by its large single bicolor flowers which are mainly pale pink-lavender with a darker lavender-pink on the edges, medium green leaves, compact habit, and by its floriferousness.

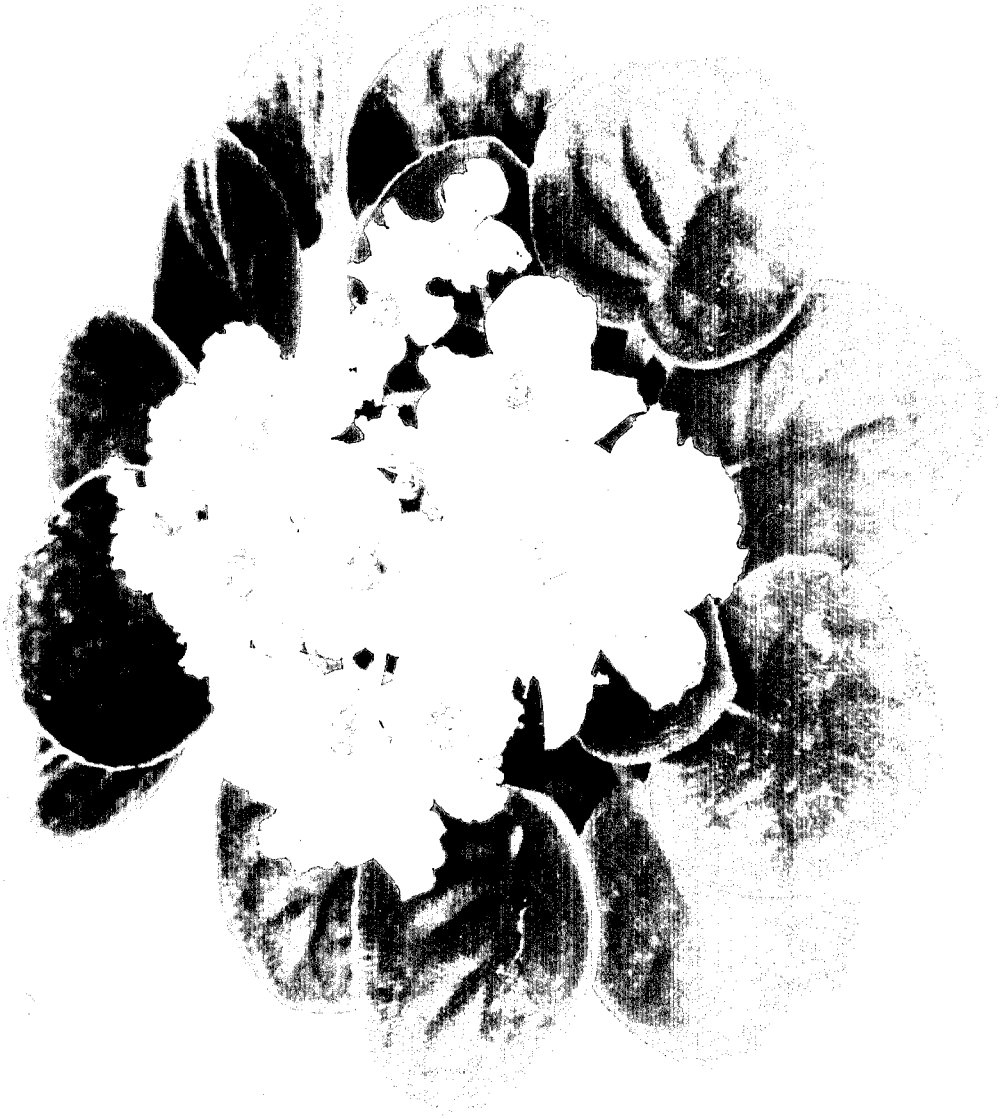

* * * * *